(12) United States Patent
Lucet-Levannier et al.

(10) Patent No.: US 7,232,839 B2
(45) Date of Patent: Jun. 19, 2007

(54) BENZOISOTHIAZOLONE COMPOSITIONS

(75) Inventors: Karine Lucet-Levannier, Reuil-Malmaison (FR); Alexandre Cavezza, Pavillon sous Bois (FR); Irene Erdelmeier, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 11/268,565

(22) Filed: Nov. 8, 2005

(65) Prior Publication Data

US 2006/0142587 A1   Jun. 29, 2006

Related U.S. Application Data

(60) Provisional application No. 60/634,984, filed on Dec. 13, 2004.

(30) Foreign Application Priority Data

Nov. 8, 2004   (FR) .................................... 04 52563

(51) Int. Cl.
- *C07D 275/04*   (2006.01)
- *C07D 275/06*   (2006.01)
- *A61K 31/428*   (2006.01)

(52) U.S. Cl. ....................................... 514/373; 548/209

(58) Field of Classification Search ................ 548/209; 514/373
See application file for complete search history.

(56) References Cited

U.S. PATENT DOCUMENTS

| | | | |
|---|---|---|---|
| 4,654,354 A | 3/1987 | Shroot et al. | |
| 5,507,862 A * | 4/1996 | Tsuboi et al. | 106/18.33 |

FOREIGN PATENT DOCUMENTS

| | | |
|---|---|---|
| EP | 0 644 243 | 3/1995 |
| EP | 1 442 737 | 8/2004 |

* cited by examiner

*Primary Examiner*—Kamal A. Saeed
*Assistant Examiner*—Michael P. Barker
(74) *Attorney, Agent, or Firm*—Oblon, Spivak, McClelland, Maier & Neustadt, P.C.

(57) ABSTRACT

A composition, suitable for topical application to the skin, containing at least one benzoisothiazolone of formula (I):

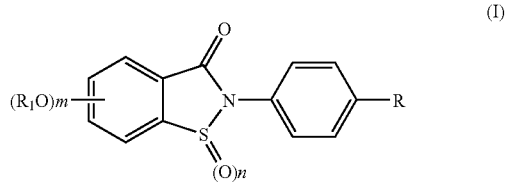

Novel benzoisothiazolones of formula (I) and a method of caring for dry and/or mature skin.

24 Claims, 3 Drawing Sheets

BENZOISOTHIAZOLONE COMPOSITIONS

REFERENCE TO PRIOR APPLICATIONS

This application claims priority to U.S. provisional application 60/634,984 filed Dec. 13, 2004, and to French patent application 0452563 filed Nov. 8, 2004, both incorporated herein by reference.

FIELD OF THE INVENTION

The present invention relates to a composition comprising at least one benzoisothiazolone of given formula, and also to a method of caring for dry and/or mature skin, comprising the topical application of the abovementioned composition to said skin. In a preferred embodiment the invention composition is suitable for topical application to the skin.

Additional advantages and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. The description is to be regarded as illustrative in nature, and not as restrictive.

BACKGROUND OF THE INVENTION

Many women, from the age of thirty-five, and more particularly after the menopause, frequently complain of dryness of their skin, and of unattractive or uncomfortable manifestations resulting therefrom (desquamation, dull complexion, cutaneous atony). Now, as is now known, this dryness is caused by a decrease in the production of sebum with age.

Sebum is the natural product of the sebaceous gland which, together with the sweat produced by the eccrine or aprocrine glands, constitutes a natural moisturizer for the epidermis. It consists essentially of a more or less complex mixture of lipids. Conventionally, the sebaceous gland produces squalene, triglycerides, aliphatic waxes, cholesterol waxes and possibly free cholesterol (Stewart, M. E., *Semin. Dermatol.* 11, 100–105 (1992)). The action of bacterial lipases converts a variable portion of the triglycerides into free fatty acids.

Sebocytes are the competent cells of the sebaceous gland. The production of sebum is associated with the programme of terminal differentiation of these cells. During this differentiation, the metabolic activity of the sebocytes is essentially focused on the biosynthesis of lipids (lipogenesis) and more specifically on the neosynthesis of fatty acids and squalene.

A compound for stimulating the production of the lipids that form sebum, by the cells of the sebaceous gland (the sebocytes), would therefore be of definite advantage for the treatment of oligoseborrheic dry skin, i.e. skin with a sebum content of less than 100 μg/cm² on the forehead.

To this end, it has been proposed in patent U.S. Pat. No. 4,496,556 to use DHEA, a steroid secreted by the adrenal glands, or its esters, administered topically, to increase the production of sebum.

However, due to regulatory matters, it is not always possible to use compounds of this type in cosmetics. In addition, its efficacy is insufficient for oligoseborrheic skin. There is thus still a need for cosmetically acceptable compounds allowing the sebaceous function to be efficiently stimulated, for the purpose of treating oligoseborrheic dry skin.

Such compounds would also be useful in the treatment of a dry scalp, which is often associated with dull, lifeless hair.

SUMMARY OF THE INVENTION

The inventors have now discovered, surprisingly, that certain benzoisothiazolones make it possible to satisfy the above need.

BRIEF DESCRIPTION OF THE DRAWINGS

Compounds of formula (I) for which R=H, $R_1$=$CH_3$ and m=1 can be prepared according to the reaction scheme illustrated in FIG. 1.

Compounds of formula (I) for which R=$OCH_3$, $R_1$=$CH_3$ and m=1 can be prepared according to the reaction scheme illustrated in FIG. 2.

Figure 3:
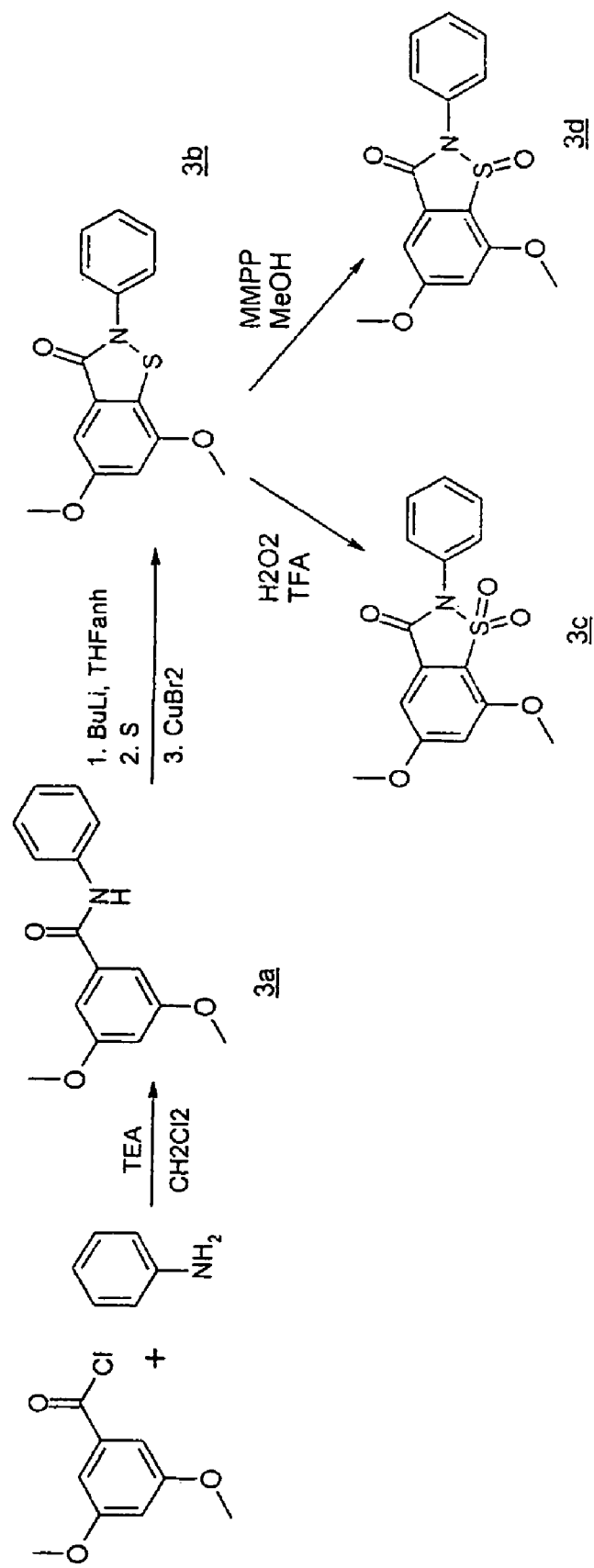

Compounds for which m=2 can be prepared according to the reaction scheme illustrated in FIG. 3.

DETAILED DESCRIPTION OF THE PREFERRED EMBODIMENTS

The benzoisothiazolones that are the subject of the present invention are part of a class of compounds that have already been described as agents intended to protect an optical recording medium against moisture (JP-10 027 381), as stabilizers in the manufacture of polycarbonate moulds, with a view to conferring, on these moulds, resistance to radiation and to hot steam (EP-0 742 260), or else as anticancer agents (JP-04 077 476).

Benzoisothiazolones very similar to those that are the subject of this invention have, moreover, been described as antibacterial and antifungal agents, for example in the local treatment of dermatophytoses (U.S. Pat. No. 3,012,039).

Some benzoisothiazolones covered by the present invention are, moreover, known to prevent the adhesion of harmful aquatic organisms to surfaces (for example of boats or of factories) exposed to water (EP-0 644 243)

Finally, N-(5-methoxy-2-phenyl)-1,2-benzoisothiazolone 1,1-dioxide is part of a chemical library (CAS No.: 632300-86-8).

Thus, a composition, in particular a cosmetic composition, suitable for topical application to the skin, comprising the benzoisothiazolones according to the invention, has never been described.

A subject of the present invention is therefore a composition, suitable for topical application to the skin, comprising at least one compound of formula (I):

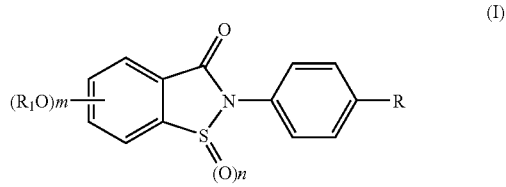

in which:

$R_1$ is a hydrogen atom or a methyl radical,

R is a hydrogen atom or a methoxy radical, m is equal to 1 or 2, n is equal to 0, 1 or 2.

According to a preferred embodiment of the invention, m is equal to 1. In this case, the $OR_1$ group is preferably located in the 4-position on the benzoisothiazolone. According to another embodiment, m is equal to 2. In this case, the $OR_1$ groups (which may be identical or different) are preferably located in the 5- and 7-positions on the benzoisothiazolone.

According to a preferred embodiment, n is equal to 2.

Included as examples of compounds that can be used in the present invention, mention may be made in particular of:

4-hydroxy-2-phenyl-1,2-benzisothiazol-3(2H)-one 4-hydroxy-2-phenyl-1,2-benzisothiazol-3(2H)-one 1-oxide 4-hydroxy-2-phenyl-1,2-benzisothiazol-3(2H)-one 1,1-dioxide 4-methoxy-2-phenyl-1,2-benzisothiazol-3(2H)-one 4-methoxy-2-phenyl-1,2-benzisothiazol-3(2H)-one 1-oxide 4-methoxy-2-phenyl-1,2-benzisothiazol-3(2H)-one 1,1-dioxide 4-hydroxy-2-(4-methoxyphenyl)-1,2-benzisothiazol-3(2H)-one 4-hydroxy-2-(4-methoxyphenyl)-1,2-benzisothiazol-3(2H)-one 1-oxide 4-hydroxy-2-(4-methoxyphenyl)-1,2-benzisothiazol-3(2H)-one 1,1-dioxide 4-methoxy-2-(4-methoxyphenyl)-1,2-benzisothiazol-3(2H)-one 4-methoxy-2-(4-methoxyphenyl)-1,2-benzisothiazol-3(2H)-one 1-oxide 4-methoxy-2-(4-methoxyphenyl)-1,2-benzisothiazol-3(2H)-one 1,1-dioxide 5,7-dihydroxy-2-phenyl-1,2-benzisothiazol-3(2H)-one 5,7-dihydroxy-2-phenyl-1,2-benzisothiazol-3(2H)-one 1-oxide 5,7-dihydroxy-2-phenyl-1,2-benzisothiazol-3(2H)-one 1,1-dioxide 5,7-dimethoxy-2-phenyl-1,2-benzisothiazol-3(2H)-one 5,7-dimethoxy-2-phenyl-1,2-benzisothiazol-3(2H)-one 1-oxide 5,7-dimethoxy-2-phenyl-1,2-benzisothiazol-3(2H)-one 1,1-dioxide 5,7-dihydroxy-2-(4-methoxyphenyl)-1,2-benzisothiazol-3(2H)-one 5,7-dihydroxy-2-(4-methoxyphenyl)-1,2-benzisothiazol-3(2H)-one 1-oxide 5,7-dihydroxy-2-(4-methoxyphenyl)-1,2-benzisothiazol-3(2H)-one 1,1-dioxide 5,7-dimethoxy-2-(4-methoxyphenyl)-1,2-benzisothiazol-3(2H)-one 5,7-dimethoxy-2-(4-methoxyphenyl)-1,2-benzisothiazol-3(2H)-one 1-oxide 5,7-dimethoxy-2-(4-methoxyphenyl)-1,2-benzisothiazol-3(2H)-one 1,1-dioxide.

The preferred compounds for use in the present invention are 4-methoxy-2-(4-methoxyphenyl)-1,2-benzisothiazol-3(2H)-one 1,1-dioxide of formula:

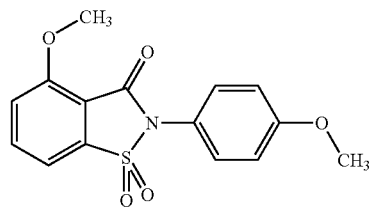

and 4-hydroxy-2-phenyl-1,2-benzisothiazol-3 (2H)-one 1,1-dioxide of formula:

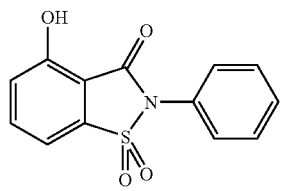

A subject of the present invention is also novel benzoisothiazolones chosen from the compounds of formula (I) above, with the exception of those for which:

n=0; R=H; m=1; and $R_1$=$CH_3$; and n=2; R=H; m=1; and $R_1$=$CH_3$.

The compounds of formula (I) for which R=H, $R_1$=$CH_3$ and m=1 can be prepared according to the reaction scheme illustrated in the attached FIG. 1, as described in Examples 1 to 3 hereinafter.

The compounds of formula (I) for which R=$R_1$=H and m=1 can be prepared according to the reaction scheme illustrated in the attached FIG. 1, as described in Example 4 hereinafter.

The compounds of formula (I) for which R=$OCH_3$, $R_1$=$CH_3$ and m=1 can be prepared according to the reaction scheme illustrated in the attached FIG. 2, as described in Examples 5 to 7 hereinafter.

The compounds of formula (I) for which R=$OCH_3$, $R_1$=H and m=1 can be prepared according to the reaction scheme illustrated in the attached FIG. 2, as described in Example 8 hereinafter.

Finally, the compounds for which m=2 can be prepared according to the reaction scheme illustrated in the attached FIG. 3, according to a process similar to that described in Examples 9 to 11 hereinafter.

The N-phenylbenzamide precursors used in these processes are either purchased, or are prepared from reacting the corresponding aniline derivative on the corresponding acyl chloride in the presence of an aminated base such as triethylamine in an aprotic solvent, for instance dichloromethane. Such is within the skill of the average artisan in view of this disclosure.

The step consisting of introduction of the sulphur and of cyclization is carried out in a single step, according to the procedure described in the publication: JOC, 1989, 54, 2964–2966.

The benzoisothiazolone oxidations are carried out with conventional reactants for the oxidation of sulphur, i.e. $H_2O_2$/trifluoroacetic acid (TFA) for the dioxides and magnesium monoperoxyphthalate hexahydrate (MMPP) or N-chlorosuccinimide (NCS) for the oxides. These methods are well known to those skilled in the art and are described in particular in references *JOC.* 2000, 65, 8439–8443; *JOC.* 2000, 65, 6462–6473 and *Bull. Chem. Soc. Jpn.* 58, 3131 (1985).

The inventors have demonstrated that a composition comprising the compounds of formula (I), for example in a physiologically acceptable medium, makes it is possible to significantly stimulate the production of the lipids that form sebum, by the cells of the sebaceous gland. This composition is therefore of advantage in caring for dry skin or a dry scalp, and more particularly in caring for mature skin. The area of skin treated with the compounds according to the invention is preferably the skin of the face and/or of the neck and/or of the hands.

A subject of the present invention is therefore also a method of caring for dry and/or mature skin, comprising the topical application of the composition defined above to the skin, in particular of the face and/or of the neck and/or of the hands.

In this regard, the invention method and composition is preferably used by subjects desirous of the benefits noted herein, subjects "in need of" these benefits. Such subjects are typically have dry and/or mature skin, such as by self diagnosis or cosmetician or medical diagnosis, or are at recognized and appreciated risk of developing such conditions and who use the invention methods and compositions to combat these effects. In this regard, the invention process can be viewed as one for delaying the onset of the appearance of, and/or for caring for or reducing the effects of dry and/or mature skin.

Naturally, one using the invention as disclosed will use an amount of the invention composition effective to care for dry and/or mature skin. Such amount is inclusive of an amount of the compositions described herein at the disclosed concentrations of active ingredients sufficient to cover the area of the skin being treated in a single application, and of course includes that amount applied upon repeated application, for example on a daily basis over a course of days, weeks, etc. In a preferred embodiment the invention process includes multiple applications of the invention composition to the area(s) of skin in need of attention.

The composition according to the invention is particularly suitable for treating oligoseborrheic dry skin, i.e. skin with a sebum content of less than. 100 μg/cm$^2$ on the forehead. This type of skin is frequently encountered in women around the time of menopause, such that the composition used according to the invention is preferably applied to women over the age of forty, preferably over the age of fifty, or even over the age of sixty.

A subject of the present invention is also the use of at least one compound of formula (I) as defined above, as an agent for relipidizing dry or mature skin.

A subject of the present invention is also the use of at least one compound of formula (I) as defined above, for preparing a composition, in particular a dermatological composition, for treating disorders associated with oligoseborrheic dry skin, in particular forms of dermatitis.

The amount of compound of formula (I) that can be used according to the invention depends, of course, on the desired effect and can thus vary to a large extent. In general, the compound of formula (I) will be present in an amount that is sufficient, to significantly increase the production of sebum, and advantageously to increase by at least 10% the production of sebum, by a culture of sebocytes, as described in Example 12 hereinafter.

To give an order of magnitude, this compound, may be used in an amount representing from 0.001 to 10% of the total weight of the composition, preferably in an amount representing from 0.1% to 5% of the total weight of the composition.

The composition according to the invention is generally suitable for topical application to the skin (respectively, the scalp) and it therefore contains a physiologically acceptable medium, i.e. a medium that is compatible with the skin (respectively, the scalp) and, optionally, with its integuments (eyelashes, nails, hair) and/or the mucous membranes. This medium is advantageously compatible with the skin of the face and/or of the neck and/or of the hands. It is preferably a cosmetically acceptable medium, i.e. a medium that does not generate any discomfort (redness, taughtness, stinging) that may put the user off the composition.

For topical application to the skin, this composition may be in any form, including any of the forms used in cosmetics and dermatology, and it may in particular be in the form of an optionally gelled oily solution, of a dispersion of the lotion type, optionally a two-phase lotion, of an emulsion obtained by dispersing a fatty phase in an aqueous phase (O/W emulsion) or vice versa (W/O emulsion), or of a triple emulsion (W/O/W or O/W/O emulsion). These compositions can be prepared according to known methods. A composition comprising water, capable of transporting hydrophilic active agents, and in particular a composition in the form of an oil-in-water emulsion, is preferably used according to this invention.

The invention composition may be more or less fluid and may have the appearance of a white or coloured cream, of an ointment, of a milk, of a lotion, of a serum, of a paste or of a mousse. It may optionally be applied in the form of an aerosol. It may also be in solid form, in particular in the form of a stick. It may be used as care product and/or as a makeup product for the skin.

When it is suitable for and intended for application to the scalp, the composition according to the invention may, as a variant, be used as a shampoo or as a conditioner.

When the composition used according to the invention is an emulsion, the proportion of the fatty phase may range for example from 5 to 80% by weight, and preferably from 5 to 50% by weight, relative to the total weight of the composition. The oils, the emulsifiers and the co-emulsifiers used in the composition in the form of an emulsion are chosen from those conventionally used in the field under consideration. The emulsifier and the co-emulsifier may be present, in the composition, in a proportion ranging for example from 0.3 to 30% by weight, and preferably from 0.5 to 20% by weight, relative to the total weight of the composition.

As oils that may be used in the invention, mention may be made of mineral oils (liquid petroleum jelly), oils of plant origin (apricot kernel oil, olive oil, soya bean oil), synthetic oils, silicone oils (cyclomethicone and dimethicones) and fluoro oils (perfluoropolyethers). Fatty alcohols (cetyl alcohol), fatty acids and waxes (carnauba wax or oxokerite) may also be used as fatty substances.

As emulsifiers and co-emulsifiers that can be used in the invention, mention may, for example, be made of fatty acid esters of polyethylene glycol such as a PEG-100 stearate, fatty acid esters of glycerol such as glyceryl stearate, sucrose esters, alkyl polyglycosides, fatty alcohol ethers of polyethylene glycol, and fatty acid esters of methyl glucose.

The composition according to the invention may also contain adjuvants such as those that are usual in cosmetics, such as hydrophilic or lipophilic gelling agents/thickeners, in particular acrylamide homopolymers and copolymers, acrylic homopolymers and copolymers, acrylamidomethylpropanesulphonic acid (AMPS) homopolymers and copolymers, and polysaccharides; hydrophilic and lipophilic active agents; preserving agents; fragrances; fillers such as silica, polyamide microspheres and polyamide fibres; pigments; and dyestuffs. The amounts of these various adjuvants include those conventionally used in the field under consideration, and, for example, from 0.01 to 20% of the total weight of the composition. Depending on their nature, these adjuvants can be introduced into the fatty phase or into the aqueous phase, as appropriate. In any event, these adjuvants, and also the proportions thereof, will be chosen so as not to harm the desired properties of the compounds of formula (I) used according to the invention.

As active agents, it will be advantageous to introduce into the composition according to the invention at least one compound chosen from: desquamating agents, moisturizers; calmatives; and agents for stimulating keratinocyte proliferation and/or differentiation.

Specifically, the stimulation of seborrhoea with the compounds of formula (I) according to the invention may, in certain individuals, provide a proliferation terrain for the resident microflora of the follicular ostium (in particular *Propionibacterium acnes*), thus resulting in considerable hydrolysis of the sebum triglycerides to free fatty acids and the reduction of the unsaturations of polyunsaturated fatty acids (in particular linoleic acid). These two phenomena may contribute towards keratinization of the infundibulum and the formation of a micro-comedone. This may degenerate into a comedone, plugging and dilating the pore in an unattractive manner. At a more advanced stage, this plug may diverge towards an inflammatory acneic lesion.

The addition of desquamating agents or agents for regulating keratinocyte proliferation or differentiation to the composition according to the invention makes it possible to avoid the formation of these comedones. Similarly, antibacterial or bacteriostatic agents would, by moderating the proliferation of the resident microflora, make it possible to obtain the same effect.

In addition, the moisturizers may complement the effect obtained using the compounds according to the invention, and the calmatives are useful for improving the comfort of oligoseborrheic dry skin.

Examples of such additional active agents are given below.

Desquamating Agents

The term "desquamating agent" is intended to mean any compound capable of acting:

either directly on the desquamation by promoting exfoliation, such as β-hydroxy acids, in particular salicylic acid and its derivatives (including 5-n-octanoylsalicylic acid); α-hydroxy acids, such as glycolic acid, citric acid, lactic acid, tartaric acid, malic acid or mandelic acid; urea; gentisic acid; oligofucoses; cinnamic acid; extract of *Saphora japonica*; resveratrol;

or on the enzymes involved in the desquamation or degradation of corneodesmosomes, glycosidases, stratum corneum chymotryptic enzyme (SCCE), or even other proteases (trypsin, chymotrypsin-like). Mention may be made of agents for chelating mineral salts: EDTA; N-acyl-N,N',N'-ethylenediaminetriacetic acid; amino-sulphonic compounds, and in particular (N-2-hydroxyethylpiperazine-N-2-ethane)sulphonic acid (HEPES); derivatives of 2-oxothiazolidine-4-carboxylic acid (procysteine); derivatives of alpha amino acids of the glycine type (as described in EP-0 852 949, and also the sodium methylglycinediacetate sold by BASF under the trade name Trilon M); honey; sugar derivatives such as O-octanoyl-6-D-maltose and N-acetylglucosamine.

Moisturizer

The term "moisturizer" is intended to mean:

either a compound that acts on the barrier function, in order to maintain the moisturization of the stratum corneum, or an occlusive compound. Mention may be made of ceramides, sphingoid-based compounds, lecithins, glycosphingolipids, phospholipids, cholesterol and its derivatives, phytosterols (stigmasterol, β-sitosterol, campesterol), essential fatty acids, 1,2-diacylglycerol, 4-chromanone, pentacyclic triterpenes such as ursolic acid, petroleum jelly and lanolin;

or a compound that directly increases the water content of the stratum corneum, such as threalose and its derivatives, hyaluronic acid and its derivatives, glycerol, pentanediol, sodium pidolate, serine, xylitol, sodium lactate, polyglycerol acrylate, ectoin and its derivatives, chitosan, oligosaccharides and polysaccharides, cyclic carbonates, N-lauroylpyrrolidonecarboxylic acid and N-α-benzoyl-L-arginine;

or a compound that activates the sebaceous glands, such as DHEA and its derivatives, and vitamin D and its derivatives.

Agents for Stimulating Keratinocyte Proliferation and/or Differentiation

The agents for stimulating keratinocyte proliferation that can be used in the composition according to the invention comprise in particular retinoids such as retinol and its esters, including retinyl palmitate; phloroglucinol; the walnut cake extracts sold by the company Gattefosse; and the *Solanum tuberosum* extracts sold by the company Sederma.

Retinoids are preferred for use in this invention, in particular retinol and its esters.

The agents for stimulating keratinocyte differentiation comprise, for example, minerals such as calcium; the extract of lupin sold by the company Silab under the trade name Photopréventine®; sodium beta-sitosteryl sulphate sold by the company Seporga under the trade name Phytocohésine®; and the extract of corn sold by the company Solabia under the trade name Phytovityl®.

Calmatives

Among the materials that are effective as calmatives, mention may be made, in a non-limiting manner, of the following active agents; pentacyclic triterpenes, such as β-glycyrrhetinic acid and its salts and/or its derivatives (glycyrrhetic acid monoglucuronide, stearyl glycyrrhetinate, 3-stearoyloxyglycyrrhetic acid), ursolic acid and its salts, oleanolic acid and its salts, betulinic acid and its salts, extracts of *Paeonia suffruticosa* and/or *lactiflora*, of *Rosmarinus officinalis*, of epilobium, of *Pygeum*, of *Boswellia serrata*, of *Centipeda cunnighami*, of *Helianthus annuus*, of *Cola nitida*, of clove and of *Bacopa moniera*; salicylic acid salts, and in particular zinc salicylate; extracts of algae, in particular of *Laminaria saccharina*; Canola oil, Tamanu oil, beauty-leaf oil, omega-3-unsaturated oils such as musk rose oil, blackcurrant oil, ecchium oil, fish oil; α-bisabolol and extracts of camomile; allantoin; the phosphoric diester of vitamins E and C; capryloyl-glycine; tocotrienols; piperonal; *Aloe vera*; phytosterols; cortisone, hydrocortisone, indomethacin and betamethasone.

Mention may also be made of substance P antagonists, and in particular: strontium salts; spring waters and in particular the spring water of the Vichy basin and the spring water of La Roche Posay; bacterial extracts and in particular the extract of non-photosynthetic filamentous bacteria described in patent application EP-0 761 204, preferably prepared from bacteria belonging to the order Beggiatoales, and more particularly to the genus *Vitreoscilla*. Preferably, a strain of *Vitreoscilla filiformis* is used according to the invention.

Mention may also be made of CGRP antagonists, and in particular an extract of (preferably undifferentiated) cells of at least one plant of the family Iridaceae, obtained by in vitro culturing. The Iridacea plant preferably belongs to the genus *Iris*. In particular, it is preferred to use an aqueous extract of *Iris pallida*, as described in application EP-0 765 668.

Finally, mention may be made of bradykinin antagonists, and in particular an extract of at least one plant of the family Rosaceae, preferably cultivated in vivo. Preferably, a plant belonging to the genus *Rosa*, advantageously of the species *Rosa gallica*, more preferably an aqueous-glycolic extract of *Rosa gallica* petals, as described in patent application EP-0 909 556, is used according to the invention.

Antibacterial Agents

The antibacterial agents that can be used in the present invention may in particular be chosen from 2,4,4'-trichloro-2'-hydroxydiphenyl ether (or triclosan), 3,4,4'-trichlorobanilide, phenoxyethanol, phenoxypropanol, phenoxyisopropanol, hexamidine isethionate, metronidazole and its salts, miconazole and its salts, itraconazole, terconazole, econazole, ketoconazole, saperconazole, fluconazole, clotrimazole, butoconazole, oxiconazole, sulphaconazole, sulconazole, terbinafine, ciclopirox, ciclopiroxolamine, undecylenic acid and its salts, benzoyl peroxide, 3-hydroxybenzoic acid, 4-hydroxybenzoic acid, phytic acid, N-acetyl-L-cysteine acid, lipoic acid, azelaic acid and its salts, arachidonic acid, resorcinol, 2,4,4'-trichloro-2'-hydroxydiphenyl ether, 3,4,4'-trichlorocarbanalide, octopirox, octoxyglycerine, octanoylglycine, caprylyl glycol, 10-hydroxy-2-decanoic acid, dichlorophenyl imidazole dioxolane and its derivatives, described in patent WO 93/18743, farnesol and phytosphingosines, and mixtures thereof.

The preferred antibacterial agents are triclosan, phenoxyethanol, octoxyglycerine, octanoylglycine, 10-hydroxy-2-decanoic acid, caprylyl glycol, farnesol and azelaic acid.

Figure 1:
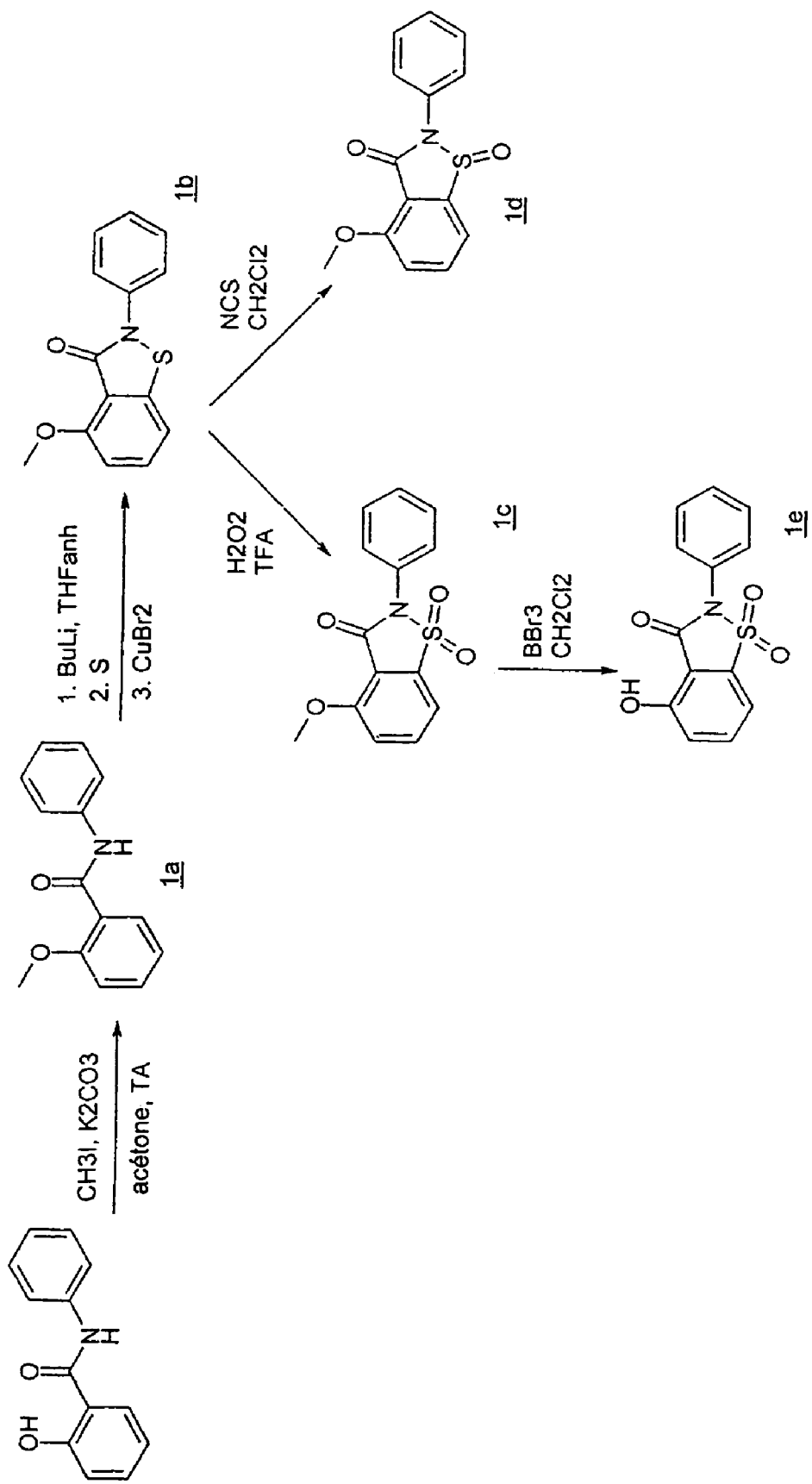
Figure 2:
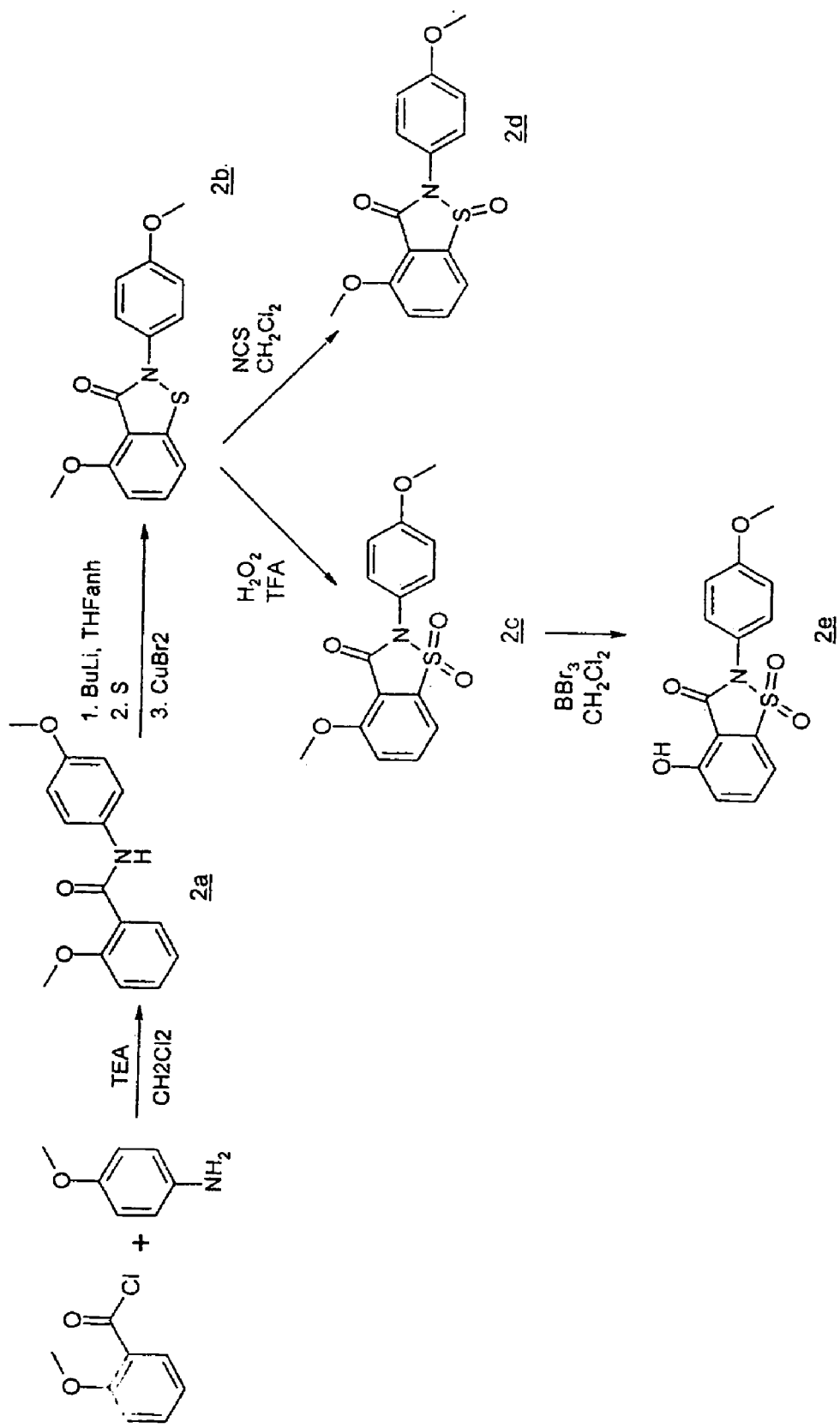

The invention will now be illustrated with the following non-limiting examples, which refer to the attached FIGS. 1 to 3 in which the processes for preparing the compounds mentioned in these examples are represented.

EXAMPLES

Example 1

Synthesis of 4-methoxy-2-phenyl-1,2-benzisothiazol-3(2H)-one

First Step

As illustrated in FIG. 1, 10 g of salicylanilide (0.0469 mol, 1 eq) and then 12.96 g of potassium carbonate (0.0938 mol, 2 eq) are placed in a 500 ml three-necked flask. 235 ml of acetone are added. 3.51 ml of iodomethane (0.0563 mol, 1.2 eq) are added dropwise. The mixture is left to stir at ambient temperature for 18 hours.

The white precipitate formed is filtered off and the filtrate evaporated under reduced pressure (P=200 mbar, T=40° C.). The oil obtained is taken up in 150 ml of ethyl acetate and washed with 3×50 ml of water and 50 ml of saturated aqueous sodium chloride solution. The organic phase is dried over sodium sulphate, filtered, and evaporated under reduced pressure. (P=220 mbar, T=40° C.).

The product is dried under vacuum in the presence of diphosphorus pentoxide so as to obtain 9.8 g of 2-methoxy-N-phenylbenzamide (1a), in the form of a white wax.

Second Step 6 g of protected 2-methoxy-N-phenylbenzamide (1a) (0.026 mol, 1 eq) are placed in a 500 ml three-necked flask dried beforehand in an oven (T=115° C.) and placed under argon. 180 ml of anhydrous tetrahydrofuran are added and this solution is then cooled to 0° C. 30.2 ml of n-butyl lithium titred at 1.75 mol/l (0.052 mol, 2 eq) are added dropwise. The mixture is allowed to stir at 0° C. for 45 minutes and then 0.846 g of sublimated sulphur (0.026 mol, 1 eq) is added. The stirring is continued at 0° C. for 30 minutes and the reaction mixture is then brought to T=−56° C. using an acetone+dry ice bath. 11.6 g of anhydrous copper bromide (0.052 mol, 2 eq) are added. The mixture is left to stir at −56° C. for 30 minutes and then at ambient temperature for 18 hours.

The reaction mixture is poured into 150 ml of saturated aqueous ammonium chloride solution. After filtration through celite 545, extraction is carried out with 3×150 ml of ethyl acetate and the organic phases are then washed with 100 ml of a saturated aqueous sodium chloride solution. The organic phase is dried over magnesium sulphate, filtered, and then evaporated under reduced pressure (P=220 mbar, 40° C.).

The compound (1b) or 4-methoxy-2-phenyl-1,2-benzisothiazol-3(2H)-one (m=1.8 g) is obtained by chromatography on a silica gel column (eluent: cyclohexane/ethyl acetate: 7/3), in the form of a white solid. The $^1$H NMR and mass spectrometry analyses are in accordance with the expected structure.

Comment: the disulphide compound is also isolated and may be used in the step consisting of S-oxidation to sulphonamide.

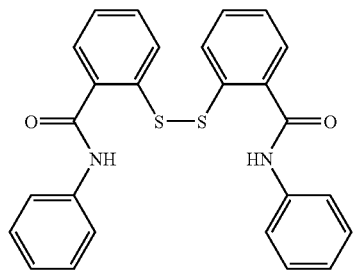

Example 2

Synthesis of 4-methoxy-2-phenyl-1,2-benzisothiazol-3(2H)-one 1,1-dioxide

As illustrated in FIG. 1, 1.15 g of compound (1a) (0.0045 mol, 1 eq—80% pure) obtained in Example 1 above is introduced into a 100 ml round-bottomed flask, followed by 17.1 ml of trifluoroacetic acid (0.223 mol, 50 eq) and 1.86 ml of 30% hydrogen peroxide (0.0178 mol, 4 eq). The mixture is left to stir at ambient temperature for 18 hours.

The reaction medium is diluted with 80 ml of dichloromethane and washed with 2×80 ml of water, 2×50 ml of a saturated aqueous sodium bicarbonate solution, 50 ml of water, and then 50 ml of a saturated aqueous sodium chloride solution. The organic phase is dried over magnesium sulphate, filtered, and evaporated under reduced pressure (P=220 mbar, T=40° C.).

0.83 g of compound (1c) or 4-methoxy-2-phenyl-1,2,-benzisothiazol-3(2H)-one 1,1-dioxide is obtained, in the form of a beige solid, after drying under reduced pressure (P=10$^{-1}$ mbar, ambient temperature). The $^1$H NMR and mass spectrometry analyses are in accordance with the expected structure.

Example 3

Synthesis of 4-methoxy-2-phenyl-1,2-benzisothiazol-3(2H)-one 1-oxide

As illustrated in FIG. 1, 0.355 g of N-chlorosuccinimide (0.0026 mol, 1 eq) and 50 ml of dichloromethane are introduced into a 250 ml three-necked flask. This solution is cooled to 0° C. and then 0.685 g of compound (1b) obtained in Example 1 and solubilized in 25 ml of dichloromethane is added dropwise in 45 minutes. The reaction mixture is allowed to return to ambient temperature and the stirring is maintained for 3 hours.

100 ml of solution of 8 g of sodium hydrogen carbonate in water are added. The mixture is stirred at ambient temperature for 1 hour. The organic phase is washed with 2×50 ml of water and then 50 ml of a saturated aqueous sodium chloride solution. The organic phase is dried over sodium sulphate, filtered, and evaporated under reduced pressure (P=220 mbar, T=40° C.).

0.7 g of compound (1d) or 4-methoxy-2-phenyl-1,2-benzisothiazol-3(2H)-one 1-oxide is obtained, in the form of a beige solid, after drying under reduced pressure (P=10$^{-1}$ mbar, ambient temperature). The $^1$H NMR and mass spectrometry analyses are in accordance with the expected structure.

Example 4

Synthesis of 4-hydroxy-2-phenyl-1,2-benzisothiazol-3(2H)-one 1,1-dioxide

As illustrated in FIG. 1, 0.5 g of compound (1c) obtained in Example 2 is introduced into a 100 ml three-necked flask dried in an oven (T=115° C.) and then placed under argon. 50 ml of anhydrous dichloromethane are added and the reaction mixture is then cooled to 0° C. Boron tribromide in solution in dichloromethane at 1M is added dropwise. The mixture is left to stir at 0° C. for 3h.

The reaction medium is subsequently poured into 100 ml of water and the stirring is maintained for 30 minutes. The organic phase is washed with 2×50 ml of a saturated aqueous sodium bicarbonate solution and then 2×50 ml of saturated aqueous sodium chloride solution. The aqueous phase is dried over sodium sulphate, filtered, and evaporated under reduced pressure (P=220 mbar, T=40° C.), and results in a beige solid being obtained. The latter is taken up with 20 ml of pentane with stirring, and is then filtered so as to obtain 0.4 g of beige solid (1e) or 4-hydroxy-2-phenyl-1,2-benzisothiazol-3(2H)-one 1,1-dioxide, after drying under reduced pressure (P=10$^{-1}$ mbar, ambient temperature). The $^1$H NMR and mass spectrometry analyses are in accordance with the expected structure.

Example 5

Synthesis of 4-methoxy-2-(4-methoxyphenyl)-1,2-benzisothiazol-3(2H)-one

First Step

As illustrated in FIG. 2, 5.6 g of 2-methoxybenzoic acid chloride (0.033 mol, 1.1 eq) are dissolved in 20 ml of dichloromethane, in a 50 ml three-necked flask, and then 4.6 ml of triethylamine (0.033 mol, 1.1 eq) are added. The reaction mixture is cooled to 0–50° C. A solution of 3.7 g of p-anisidine (0.03 mol, 1 eq) in dichloromethane is added dropwise in 15 minutes. The mixture is left to stir for 1 hour at 0° C. and then at ambient temperature for 18 hours.

The mixture is taken up in 100 ml of dichloromethane, and washed with 3×50 ml of water and then 50 ml of a saturated aqueous sodium chloride solution. The organic phase is dried over magnesium sulphate, filtered, and evaporated under reduced pressure (P=220 mbar, T=40° C.).

The expected product is obtained by crystallization from toluene at −15° C. for 2 hours. 2.8 g of compound (2a) or 2-methoxy-N-(4-methoxyphenyl)benzamide are isolated, in the form of a beige solid, which is subsequently purified by chromatography on a silica gel (eluent: cyclohexane/ethyl acetate: 1/1). The $^1$H NMR and mass spectrometry analyses are in accordance with the expected structure.

Second step: The compound (2b) 4-methoxy-2-(4-methoxyphenyl)-1,2-benzisothiazol-3(2H)-one is obtained (yield=20%), in the form of a yellow liquid, by following the procedure described in the second step of Example 1 and after purification by chromatography on a silica gel column (eluent: cyclohexane/ethyl acetate: 1/1). The $^1$H NMR and mass spectrometry analyses are in accordance with the expected structure.

Comment: One of the impurities isolated is the following dimer:

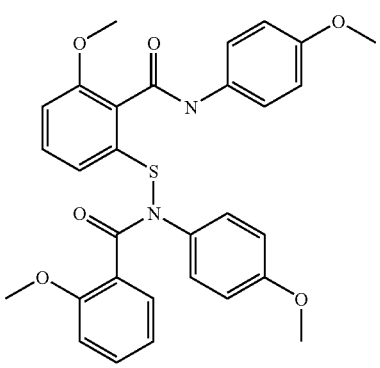

Example 6

Synthesis of 4-methoxy-2-(4-methoxyphenyl)-1,2-benzisothiazol-3(2H)-one 1,1-dioxide As illustrated in FIG. 2, the compound (2b) obtained as described in Example 5 can be used in a process similar to that described in Example 2 so as to obtain the compound (2c) or 4-methoxy-2-(4-methoxyphenyl)-1,2-benzisothiazol-3(2H)-one 1,1-dioxide, which can be isolated in the form of a white solid after purification by chromatography on a silica gel column (eluent: cyclohexane/ethyl acetate: 1/1). The $^1$H NMR and mass spectrometry analyses are in accordance with the expected structure.

Example 7

Synthesis of 4-methoxy-2-(4-methoxyphenyl)-1,2-benzisothiazol-3(2H)-one 1-oxide

As illustrated in FIG. 2, the compound. (2b) obtained as described in Example 5 can be used in a process similar to that described in Example 3 so as to obtain the compound (2d) or 4-methoxy-2-(4-methoxyphenyl)-1,2-benzisothiazol-3(2H)-one 1-oxide in the form of a beige solid. The $^1$H NMR and mass spectrometry analyses are in accordance with the expected structure.

Example 8

Synthesis of 4-hydroxy-2-(4-methoxyphenyl)-1,2-benzisothiazol-3(2H)-one 1,1-dioxide As illustrated in FIG. 2, the compound (2e) or 4-hydroxy-2-(4-methoxyphenyl)-1,2-benzisothiazol-3(2H)-one 1,1-dioxide can be obtained from the compound (2c) obtained in Example 6, by carrying out a process similar to that described in Example 4. A beige solid is obtained. The $^1$H NMR and mass spectrometry analyses are in accordance with the expected structure.

Example 9

Synthesis of 5,7-dimethoxy-2-phenyl-1,2-benzisothiazol-3(2H)-one

First Step

As illustrated in FIG. 3, 6.3 g of 3,5-dimethoxybenzoyl chloride (0.031 mol, 1 eq) are introduced into 60 ml of anhydrous dichloromethane, in a 250 ml three-necked flask under an inert atmosphere. 9.6 ml of triethylamine (0.068 mol, 2.2 eq) are added dropwise. The reaction mixture is cooled to 0–5° C. 4.05 g of aniline.HCl (0.031 mol, 1 eq) are added gradually in 30 minutes. The mixture is left to stir for 1 hour at 0° C. and then at ambient temperature for 18 hours.

The reaction mixture is taken up in 150 ml of dichloromethane and then washed with 2×100 ml of water, 100 ml of a 0.5 N hydrochloric acid solution, 2×100 ml of water and then 100 ml of a saturated aqueous sodium chloride solution. The organic phase is dried over sodium sulphate, filtered, and evaporated under reduced pressure (P=220 mbar, T=40° C.). 4.5 g of compound (3a) or 3,5-dimethoxy-N-phenyl-benzamide are obtained, in the form of a white solid. The $^1$H NMR and mass spectrometry analyses are in accordance with the expected structure.

Second Step

The procedure described in the second step of Example 1 is followed so as to form and isolate the compound involved (3b) or 5,7-dimethoxy-2-phenyl-1,2-benzisothiazol-3(2H)-one from the compound (3a) obtained in the first step above. A white solid is obtained. The $^1$H NMR and mass spectrometry analyses are in accordance with the expected structure.

Example 10

Synthesis of 5,7-dimethoxy-2-phenyl-1,2-benzisothiazol-3(2H)-one 1,1-dioxide

As illustrated in FIG. 3, the product. (3c) or 5,7-dimethoxy-2-phenyl-1,2-benzisothiazol-3(2H)-one 1,1-dioxide, as a mixture with the corresponding sulphinamide compound (3d), in a 70/30 proportion, is formed in the presence of trifluoroacetic acid and of 30% hydrogen peroxide according to the procedure described in Example 2.

The compound (3c) can be purified by chromatography on a silica gel column (eluent: cyclohexane/ethyl acetate: 8/2). A white solid is obtained. The $^1$H NMR and mass spectrometry analyses are in accordance with the expected structure.

Example 11

Synthesis of 5,7-dimethoxy-2-phenyl-1,2-benzisothiazol-3(2H)-one 1-oxide

As illustrated in FIG. 3, in a dry 50 ml two-necked flask, under $N_2$, 0.2 g of 5,7-dimethoxy-2-phenyl-1,2-benzisothiazol-3(2H)-one (0.0007 mol, 1 eq) (3b) obtained in Example 9 is solubilized in 2 ml of dichloromethane and then 10 ml of methanol are added. The reaction medium is cooled to 0° C. 0.172 g of technical grade magnesium monoperoxyphthalate hexahydrate at 80% (0.00035 mol, 0.5 eq) is added. The stirring is maintained at 0° C. for 3 hours and then at ambient temperature for 18 hours.

In order to completely consume the reactant involved (3b), the reaction medium is again cooled to 0° C., and a further 0.5 eq of technical grade magnesium monoperoxyphthalate hexahydrate at 80% is added. The stirring is, maintained at 0° C. for 30 minutes and then the mixture is allowed to return to ambient temperature.

The white precipitate is filtered off, and then the filtrate is concentrated under reduced pressure (P=220 mbar, T=40° C.). This reaction crude is taken up in 50 ml of dichloromethane and then washed with 25 ml of water, 25 ml of a saturated aqueous sodium bicarbonate solution, then 3×25 ml of water. The organic phase is dried over sodium sulphate, filtered, and evaporated under reduced pressure (P=220 mbar, T=40° C.).

After purification by chromatography on a silica gel column (eluent: cyclohexane/ethyl acetate: 7/3), 0.164 g of compound (3d) or 5,7-dimethoxy-2-phenyl-1,2-benzisothiazol-3(2H)-one 1-oxide is isolated, in the form of a white solid. The $^1$H NMR and mass spectrometry analyses are in accordance with the expected structure.

Example 12

Demonstration of the Activity of the Compounds of Formula (I) on Lipogenesis

The activity of the compounds (2c) and (1e) described above was tested on a model of immortalized human sebocytes in culture, derived from the SZ95 line described in Zouboulis, C. C., Seltmann, H., Neitzel, H. & Orfanos, C. E., Establishment and Characterization of an Immortalized Human Sebaceous Gland Cell Line, *J. Invest. Dermatol.*, 113, 1011–1020 (1999).

The test consisted in measuring the amount of lipids produced by the sebocytes of the line (at confluence), in the presence or absence of an active agent, diluted in DMSO, such that the final amount of DMSO in the culture medium is 0.1%. After treatment for 2 days, the adherent cells are treated with Nile red (1 µg/ml). The lipid content is then quantified by measuring the fluorescence of the dye (excitation/emission couple: 485–540 nm for the neutral lipids).

The tests are performed in sextuplicate and the experiment is repeated four times.

In parallel, proliferation tests (MUH) and cell viability tests (LDH) make it possible to check that the, effects obtained are not associated with an appreciable change in these biological parameters.

The results are collated in the table below:

| COMPOUND TESTED | CONCENTRATION | LIPID VARIATION (relative to the control) | Proliferation/cytotoxicity |
|---|---|---|---|
| Compound (2c) | $10^{-6}$ M | +43% | no |
| Compound (1e) | $10^{-6}$ M | +16% | no |
|  | $10^{-4}$ M | +39% | no |

As emerges from this table, the compounds according to the invention induce a significant increase in sebocyte lipogenesis.

In addition, in the same test, DHEA, tested at the concentration of $10^{-5}$ M, gave only a 13% increase in the lipid content of the sebum. The compounds according to the invention are therefore more efficient than DHEA.

Example 13

Cosmetic Composition (O/W Emulsion)

This composition is prepared in a manner that is conventional for those skilled in the art. The amounts given in this example are indicated as percentages by weight.

| | |
|---|---|
| 4-methoxy-2-(4-methoxyphenyl)-1,2-benzisothiazol-3(2H)-one 1,1-dioxide | 0.3% |
| Glyceryl stearate | 2% |
| Polysorbate 60 | 1% |
| Stearic acid | 1.4% |
| Triethanolamine | 0.7% |
| Carbomer | 0.4% |
| Olive oil | 12% |
| Liquid fraction of shea butter | 12% |
| Octyldodecanol | 6% |
| Isononyl isononanoate | 10% |
| Antioxidant | 0.05% |
| Fragrance | 0.5% |
| Preserving agent | 0.3% |
| Water qs | 100% |

This composition, applied twice daily, makes it possible to reinvigorate the sebaceous function of dry skin.

The above written description of the invention provides a manner and process of making and using it such that any person skilled in this art is enabled to make and use the same, this enablement being provided in particular for the subject matter of the appended claims, which make up a part of the original description and including a composition, suitable for topical application to the skin, comprising at least one compound of formula (I):

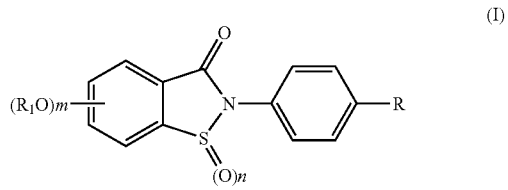

in which:
R₁ is a hydrogen atom or a methyl radical,
R is a hydrogen atom or a methoxy radical,
m is equal to 1 or 2,
n is equal to 0, 1 or 2.

As used above, the phrases "selected from the group consisting of," "chosen from," and the like include mixtures of the specified materials.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out. Terms such as "contain(s)" and the like as used herein are open terms meaning 'including at least' unless otherwise specifically noted.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

The invention claimed is:

1. A method of caring for dry and/or mature skin, comprising topically applying to dry and/or mature skin a composition comprising, in a physiologically acceptable medium, at least one compound of formula (I):

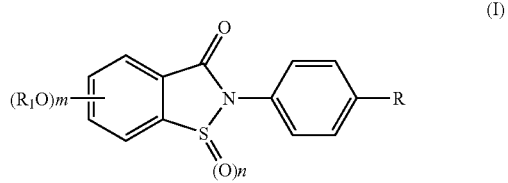

in which:
R₁ is a hydrogen atom or a methyl radical,
R is a hydrogen atom or a methoxy radical,
m is equal to 1 or 2,
n is equal to 0, 1 or 2.

2. The method according to claim 1, wherein m is equal to 1.

3. The method according to claim 1, wherein n is equal to 2.

4. The method according to claim 1, wherein the composition comprises at least one compound selected from the group consisting of:

4-hydroxy-2-phenyl-1,2-benzisothiazol-3(2H)-one;

4-hydroxy-2-phenyl-1,2-benzisothiazol-3(2H)-one 1-oxide;

4-hydroxy-2-phenyl-1,2-benzisothiazol-3(2H)-one 1,1-dioxide;

4-methoxy-2-phenyl-1,2-benzisothiazol-3(2H)-one;

4-methoxy-2-phenyl-1,2-benzisothiazol-3(2H)-one 1-oxide;

4-methoxy-2-phenyl-1,2-benzisothiazol-3(2H)-one 1,1-dioxide;

4-hydroxy-2-(4-methoxyphenyl)-1,2-benzisothiazol-3(2H)-one;

4-hydroxy-2-(4-methoxyphenyl)-1,2-benzisothiazol-3(2H)-one 1-oxide;

4-hydroxy-2-(4-methoxyphenyl)-1,2-benzisothiazol-3(2H)-one 1,1-dioxide;

4-methoxy-2-(4-methoxyphenyl)-1,2-benzisothiazol-3(2H)-one;

4-methoxy-2-(4-methoxyphenyl)-1,2-benzisothiazol-3(2H)-one 1-oxide;

4-methoxy-2-(4-methoxyphenyl)-1,2-benzisothiazol-3(2H)-one 1,1-dioxide;

5,7-dihydroxy-2-phenyl-1,2-benzisothiazol-3(2H)-one;

5,7-dihydroxy-2-phenyl-1,2-benzisothiazol-3(2H)-one 1-oxide;

5,7-dihydroxy-2-phenyl-1,2-benzisothiazol-3(2H)-one 1,1-dioxide;

5,7-dimethoxy-2-phenyl-1,2-benzisothiazol-3(2H)-one;

5,7-dimethoxy-2-phenyl-1,2-benzisothiazol-3(2H)-one 1-oxide;

5,7-dimethoxy-2-phenyl-1,2-benzisothiazol-3(2H)-one 1,1-dioxide;

5,7-dihydroxy-2-(4-methoxyphenyl)-1,2-benzisothiazol-3(2H)-one;

5,7-dihydroxy-2-(4-methoxyphenyl)-1,2-benzisothiazol-3(2H)-one 1-oxide;

5,7-dihydroxy-2-(4-methoxyphenyl)-1,2-benzisothiazol-3(2H)-one 1,1-dioxide;

5,7-dimethoxy-2-(4-methoxyphenyl)-1,2-benzisothiazol-3(2H)-one;

5,7-dimethoxy-2-(4-methoxyphenyl)-1,2-benzisothiazol-3(2H)-one 1-oxide; and 5,7-dimethoxy-2-(4-methoxyphenyl)-1,2-benzisothiazol-3(2H)-one 1,1-dioxide.

5. The method according to claim 1, wherein the composition comprises 4-methoxy-2-(4-methoxyphenyl)-1,2-benzisothiazol-3(2H)-one 1,1-dioxide.

6. The method according to claim 1, wherein the composition comprises 4-hydroxy-2-phenyl-1,2-benzisothiazol-3(2H)-one 1,1-dioxide.

7. The method according to claim 1, wherein the composition comprises, in a cosmetically acceptable medium, at least one compound of formula (I).

8. The method according to claim 1, wherein the composition further comprises at least one compound selected from the group consisting of desquamating agent, a moisturizer, a calmative, an agent for promoting keratinocyte proliferation and/or differentiation, and an antibacterial agent.

9. The method according to claim 1, in wherein the composition is in the form of an oil-in-water emulsion.

10. A compound of formula (I):

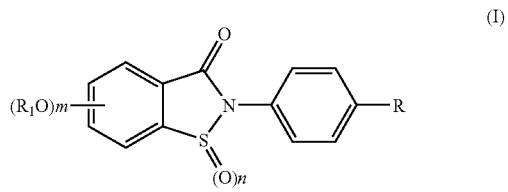

in which:
$R_1$ is a hydrogen atom or a methyl radical,
R is a hydrogen atom or a methoxy radical,
m is equal to 1 or 2, and
n is equal to 0, 1 or 2,
with the exception of those compounds for which:
n=0; R=H; m=1; and $R_1=CH_3$; and
n=2; R=H; m=1; and $R_1=CH_3$.

11. The method according to claim 1, wherein the composition is applied to the skin of women over the age of forty.

12. The method according to claim 1, wherein the composition is applied to the face and/or the neck and/or the hands.

13. The method according to claim 1, wherein the composition is applied in an amount sufficient to relipidize dry or mature skin.

14. The method according to claim 1, wherein the composition is applied in an amount sufficient to treat a disorder associated with oligoseborrheic dry skin.

15. The method according to claim 14, wherein said disorder is a form of dermatitis.

16. The compound according to claim 10, wherein m is equal to 1.

17. The compound according to claim 10, wherein n is equal to 2.

18. The compound according to claim 10, wherein the compound is selected from the group consisting of:

4-hydroxy-2-phenyl-1,2-benzisothiazol-3(2H)-one;

4-hydroxy-2-phenyl-1,2-benzisothiazol-3(2H)-one 1-oxide;

4-hydroxy-2-phenyl-1,2-benzisothiazol-3(2H)-one 1,1-dioxide;

4-methoxy-2-phenyl-1,2-benzisothiazol-3(2H)-one 1-oxide;

4-methoxy-2-phenyl-1,2-benzisothiazol-3(2H)-one 1,1-dioxide;

4-hydroxy-2-(4-methoxyphenyl)-1,2-benzisothiazol-3(2H)-one;

4-hydroxy-2-(4-methoxyphenyl)-1,2-benzisothiazol-3(2H)-one 1-oxide;

4-hydroxy-2-(4-methoxyphenyl)-1,2-benzisothiazol-3(2H)-one 1,1-dioxide;

4-methoxy-2-(4-methoxyphenyl)-1,2-benzisothiazol-3(2H)-one;

4-methoxy-2-(4-methoxyphenyl)-1,2-benzisothiazol-3(2H)-one 1-oxide;

4-methoxy-2-(4-methoxyphenyl)-1,2-benzisothiazol-3(2H)-one 1,1-dioxide;

5,7-dihydroxy-2-phenyl-1,2-benzisothiazol-3 (2H)-one;

5,7-dihydroxy-2-phenyl-1,2-benzisothiazol-3(2H)-one 1-oxide;

5,7-dihydroxy-2-phenyl-1,2-benzisothiazol-3(2H)-one 1,1-dioxide;

5,7-dimethoxy-2-phenyl-1,2-benzisothiazol-3 (2H)-one;
5,7-dimethoxy-2-phenyl-1,2-benzisothiazol-3 (2H)-one 1-oxide;
5,7-dimethoxy-2-phenyl-1,2-benzisothiazol-3 (2H)-one 1,1-dioxide;
5,7-dihydroxy-2-(4-methoxyphenyl)-1,2-benzisothiazol-3 (2H)-one;
5,7-dihydroxy-2-(4-methoxyphenyl)-1,2-benzisothiazol-3 (2H)-one 1-oxide;
5,7-dihydroxy-2-(4-methoxyphenyl)-1,2-benzisothiazol-3 (2H)-one 1,1-dioxide;
5,7-dimethoxy-2-(4-methoxyphenyl)-1,2-benzisothiazol-3 (2H)-one;
5,7-dimethoxy-2-(4-methoxyphenyl)-1,2-benzisothiazol-3 (2H)-one 1-oxide; and
5,7-dimethoxy-2-(4-methoxyphenyl)-1,2-benzisothiazol-3(2H)-one 1,1-dioxide.

19. The compound according to claim 10, wherein the compound is 4-methoxy-2-(4-methoxyphenyl)-1,2-benzisothiazol-3 (2H)-one 1,1-dioxide.

20. The compound according to claim 10, wherein the compound is 4-hydroxy-2-phenyl-1,2-benzisothiazol-3 (2H)-one 1,1-dioxide.

21. A composition comprising, in a cosmetically acceptable medium, at least one compound according to claim 10.

22. The composition according to claim 21, further comprising at least one compound selected from the group consisting of a desquamating agent, a moisturizer, a calmative, an agent for promoting keratinocyte proliferation and/or differentiation, and an antibacterial agent.

23. The composition according to claim 21, in the form of an oil-in-water emulsion.

24. A composition comprising, in a physiologically acceptable medium, at least one ingredient selected from the group consisting of mineral oils, silicone oils, fluorinated oils, hydrophilic gelling agents or thickeners, lipophilic gelling agents or thickeners, active agents, preservatives, and fragrances, and at least one compound of formula (I):

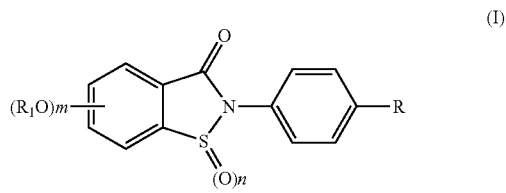

in which:
$R_1$ is a hydrogen atom or a methyl radical,
R is a hydrogen atom or a methoxy radical,
m is equal to 1 or 2,
n is equal to 0, 1 or 2.

* * * * *